United States Patent
Rathjen

(10) Patent No.: US 10,667,948 B2
(45) Date of Patent: Jun. 2, 2020

(54) DEVICE FOR PROTECTING EYE TISSUE DURING LASER TREATMENTS

(71) Applicant: Ziemer Ophthalmic Systems AG, Port (CH)

(72) Inventor: Christian Rathjen, Bremen (DE)

(73) Assignee: Ziemer Ophthalmic Systems AG, Port (CH)

( * ) Notice: Subject to any disclaimer, the term of this patent is extended or adjusted under 35 U.S.C. 154(b) by 163 days.

(21) Appl. No.: 14/949,139

(22) Filed: Nov. 23, 2015

(65) Prior Publication Data
US 2016/0143775 A1 May 26, 2016

(30) Foreign Application Priority Data
Nov. 24, 2014 (EP) ..................................... 14003938

(51) Int. Cl.
| | | |
|---|---|---|
| A61F 9/008 | (2006.01) | |
| A61B 90/00 | (2016.01) | |
| A61B 17/00 | (2006.01) | |
| A61B 18/00 | (2006.01) | |

(52) U.S. Cl.
CPC ...... *A61F 9/008* (2013.01); *A61B 2017/0019* (2013.01); *A61B 2017/00123* (2013.01); *A61B 2017/00194* (2013.01); *A61B 2018/00779* (2013.01); *A61B 2090/049* (2016.02); *A61B 2560/0487* (2013.01); *A61F 2009/00846* (2013.01); *A61F 2009/00878* (2013.01); *A61F 2009/00897* (2013.01)

(58) Field of Classification Search
CPC ............................................ A61B 2017/00123
See application file for complete search history.

(56) References Cited

U.S. PATENT DOCUMENTS

| | | | |
|---|---|---|---|
| 9,037,217 B1* | 5/2015 | Peyman | A61B 18/20 |
| | | | 600/427 |
| 2008/0033408 A1 | 2/2008 | Bueler et al. | |
| 2009/0161827 A1* | 6/2009 | Gertner | A61F 9/008 |
| | | | 378/65 |

(Continued)

FOREIGN PATENT DOCUMENTS

EP      2705812 A1     3/2014

OTHER PUBLICATIONS

May 12, 2015 (EP)—Extend European Search Report—App 14003938.9.

*Primary Examiner* — Scott Luan
(74) *Attorney, Agent, or Firm* — Banner & Witcoff, Ltd.

(57) ABSTRACT

A device for protecting tissue when treating an eye using a laser beam generated by a laser system and deflected by a scanner system comprises an eye model, a control data module and a processor. The eye model comprises eye data which define dimensions and locations of eye structures. The control data module is configured to register control data which define beam parameters of the laser beam and a scanning pattern for the laser beam. The processor is configured to simulate by computation a light spot moving on or in an eye structure on the basis of the eye data and the control data, to add up, for a plurality of measurement points of the eye structure and continuously, a beam dose emitted at the relevant measurement point by the moving light spot and to generate an emergency signal if a dose limit $D_{max}$ is exceeded at one of the measurement points.

19 Claims, 2 Drawing Sheets

(56) References Cited

U.S. PATENT DOCUMENTS

| | | | |
|---|---|---|---|
| 2010/0168724 A1* | 7/2010 | Sramek | A61F 9/008 606/13 |
| 2014/0276680 A1 | 9/2014 | Dennison et al. | |
| 2015/0141972 A1* | 5/2015 | Woodley | A61B 3/102 606/5 |
| 2015/0164689 A1 | 6/2015 | Vogel et al. | |

* cited by examiner

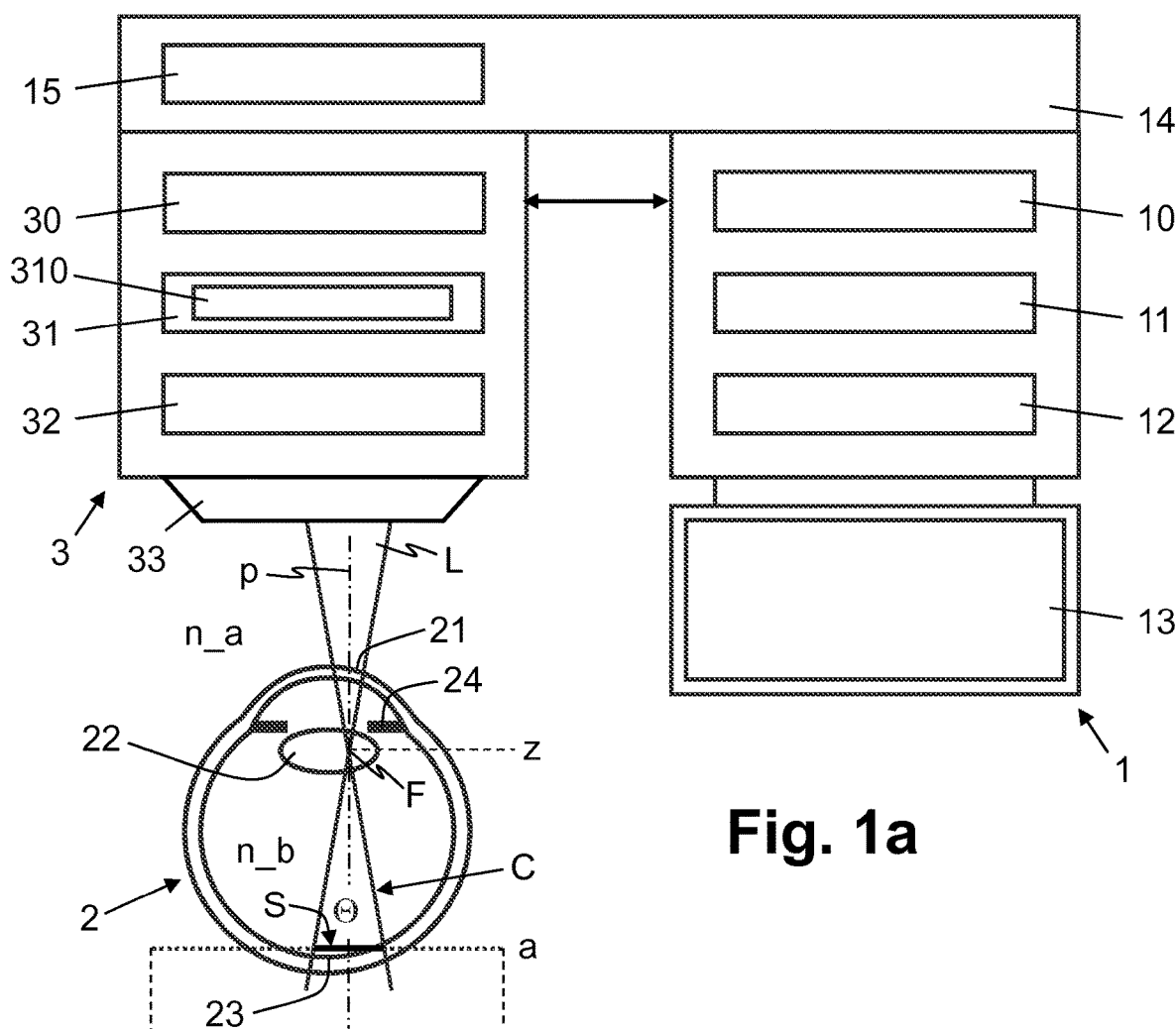
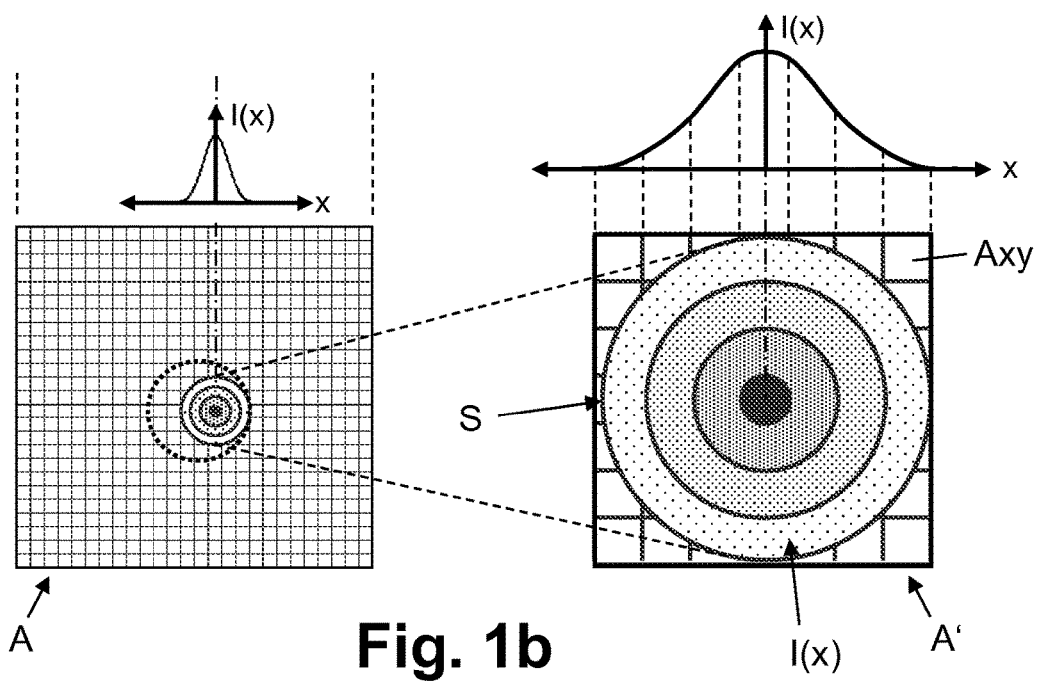
Fig. 1a
Fig. 1b

DEVICE FOR PROTECTING EYE TISSUE DURING LASER TREATMENTS

This application claims priority to European Patent Application Serial No. 14003938.9, filed Nov. 24, 2014, and entitled "DEVICE FOR PROTECTING EYE TISSUE DURING LASER TREATMENTS," the disclosure of which is incorporated by reference herein in its entirety and made part hereof.

TECHNICAL FIELD

The present invention relates to a device for protecting eye tissue during laser treatments. In particular, the present invention relates to a device for protecting tissue when treating an eye using a laser beam generated by an optical therapy system and deflected by a scanner system.

PRIOR ART

In the treatment of eye tissue, for example for refractive correction of the cornea or lens, use is made of ophthalmological laser treatment systems, which project laser radiation, in particular pulsed laser radiation, in a focused manner, e.g. onto targeted points or along a treatment line, in order thus to disintegrate tissue for ablating tissue layers or for generating tissue cuts. In preparation, the geometry and topography of the eye to be treated and the structures thereof are registered and the planned treatment is defined by means of treatment data. Since the laser beam is radiated into the eye tissue beyond the focus, there is the risk of unwanted positions in the eye being impaired by laser radiation and unintended, incorrect tissue regions or structures in the eye being treated by the laser beam and/or exposed too strongly such that damage occurs by photochemical, photo-thermal and/or photo-acoustic effects. In order to avoid such damage, limits are set for the beam energy or beam dose, which are intended to ensure the safety of the eye tissue. In accordance with US 2014/0276680, the laser energy is restricted to a maximum value in order to irradiate the retina with no more than a peak laser energy that is restricted in accordance with a safety standard, for example a safety standard pursuant to ANSI Z136.1-2000 or ISO 15004. However, the problem in this case is that the actually administered beam dose depends strongly on the employed treatment procedure and the beam parameters connected therewith, e.g. a level of beam power or numerical aperture (NA), on dynamic changes of beam parameters, focal depth, on dynamic changes of the focal depth, spot dimension, on dynamic changes of the spot dimension and/or on the scanning pattern, and so it is impossible to determine the local beam dose, and hence, in particular, the maximum local beam dose, using analytical methods since it is not possible to derive sufficiently exact calculation methods. By way of example, when applying optical therapy systems with scanning laser systems to a cataract treatment, the diameter of the light spot on the retina generated by the laser radiation changes strongly with focal depth. By contrast, such strong dependencies do not exist in the case of therapy systems for cuts in the cornea. Therefore, all relevant parameters need to be assumed to be in their most negative form in a worst-case approach in order to respect laser standards. This restricts the achievable performance of the treatment systems and methods, as a result of which, for example, the treatment time is unnecessarily lengthened because the mean power needs to be restricted in a worst-case approach. Therefore, the patient is exposed to longer vacuum times and there additionally is an increased risk of aborting the treatment since a patient can only hold still for restricted period of time. Moreover, it is also not possible to let the user carry out the definition of cuts or whole treatment procedures since the latter generally cannot monitor the observance of admissible (maximum) dose values, since this is too complicated.

SUMMARY OF THE INVENTION

It is an object of the present invention to propose a device for protecting eye tissue during laser treatments which does not have at least some of the disadvantages of the known systems. In particular, it is an object of the present invention to propose a device for protecting eye tissue during laser treatments which, to this end, enables a reliable observance of beam dose limits without needing to set, in a fixed manner, all system parameters to safety values for worst-case scenarios.

In accordance with the present invention, these objects are achieved by the features of the independent claim. Further advantageous embodiments moreover emerge from the dependent claims and the description.

A device for protecting tissue when treating an eye using a laser beam generated by an optical therapy system and deflected by a scanner system comprises an eye model comprising eye data which define dimensions and locations of eye structures, and a control data module configured to register control data which define beam parameters of the laser beam and a scanning pattern for the laser beam.

In particular, the aforementioned objects are achieved by the present invention by virtue of said device for protecting tissue moreover comprising a processor configured to simulate by computation a light spot moving on or in an eye structure on the basis of the eye data and the control data, to add up, for a plurality of measurement points of the eye structure and continuously with the moving light spot, a beam dose emitted at the relevant measurement point by the moving light spot and to generate an emergency signal if a dose limit $D_{max}$ is exceeded at one of the measurement points.

By simulating the light spot moving in accordance with the planned or executed laser treatment and by accumulating the laser energy irradiated at specific measurement points in the eye in the process, a realistic determination of the beam dose with a high spatial resolution in the eye is made possible (on and in eye structures and the surfaces thereof), which, in comparison with worst-case approaches, in which laser, eye and treatment parameters are assumed in the most negative form thereof in order to observe safety standards, enables the use of higher mean laser powers and, accompanying this, shorter treatment times while simultaneously observing safety standards.

In one embodiment variant, the control data define a scanning speed for the optical therapy system and the processor is configured to simulate the moving light spot with a movement speed based on the scanning speed.

In one embodiment variant, the beam parameters comprise the current beam power of the laser beam and the processor is configured to add up the beam dose (or irradiation dose) at the measurement points, respectively as an energy value, by integrating the beam power of the laser beam from the light spot moving over the relevant measurement point.

In one embodiment variant, the processor is configured to establish, for the measurement points of the eye structure and continuously, an irradiation time resulting by the moving light spot and to define the dose limit $D_{max}$ for the measurement points respectively in a manner dependent on the irradiation time at the relevant measurement point.

In one embodiment variant, the processor is configured to define the dose limit $D_{max}$ for the measurement points in a manner dependent on the wavelength or wavelengths of the laser beam.

In one embodiment variant, the processor is configured to determine the dose limit $D_{max}$ for the measurement points in a manner dependent on an irradiation time at the relevant measurement point.

In one embodiment variant, the processor is configured to calculate the dose limit $D_{max}$ for the measurement points according to the equation $D_{max}=C \cdot t^{3/4}$ in each case, where C is a constant dependent on the beam parameters (in particular wavelength, pulse length/pulse duration and divergence angle) of the laser beam and t is the irradiation time at the relevant measurement point.

In one embodiment variant, the processor is configured to simulate the deflected laser beam on the basis of the scanning pattern defined by the control data, to model the eye structure on the basis of the eye data, and to simulate the moving light spot on the basis of the simulated deflected laser beam and the modeled eye structure.

In one embodiment variant, the processor is configured to establish the moving light spot on a surface of the eye structure and to add up the beam dose resulting from the moving light spot for a plurality of measurement points on the surface of the eye structure.

In one embodiment variant, the processor is configured to determine the moving light spot and the measurement points on a surface of one or more eye structures from the following list: epithelium, endothelium, iris, sclera, front lens surface, rear lens surface and retinal surface.

In one embodiment variant, the device is connected to the optical therapy system and the scanner system and the processor is configured to register the control data from the optical therapy system and from the scanning system during the treatment of the eye and to transmit the emergency signal for interrupting the treatment to the optical therapy system.

In one embodiment variant, the processor is configured to register the control data for simulating the treatment of the eye by way of a user interface and to output the emergency signal as a warning notification by way of the user interface.

In one embodiment variant, the control data define one or more beam parameters from the following list: average beam power, pulse width, pulse rate, pulse energy, pulse intensity, focal size, laser beam intensity profile and divergence of the laser beam provided for the focused projection, and the processor is configured to simulate the moving light spot on the basis of the one or more beam parameters.

In one embodiment variant, the device moreover comprises a measurement system configured to determine the eye data during the treatment of the eye.

In one embodiment variant, the device moreover comprises a positioning system configured to determine a relative position of the eye during the treatment and to position the eye model relative to the optical therapy system in a manner dependent on the relative position.

BRIEF DESCRIPTION OF THE DRAWINGS

Below, an embodiment of the present invention is described on the basis of an example. The example of the embodiment is illustrated by the following attached figures:

FIG. 1a: schematically shows a cross section of an eye under treatment by a laser beam generated by an optical therapy system and deflected by a scanner system, and a device for protecting tissue during the treatment of the eye.

FIG. 1b: shows an intensity profile in the beam cross section of the laser beam and, in the top view, a light spot corresponding to the intensity profile on a (virtual) array positioned in the vicinity of the retina.

WAYS OF IMPLEMENTING THE INVENTION

Figure 2:
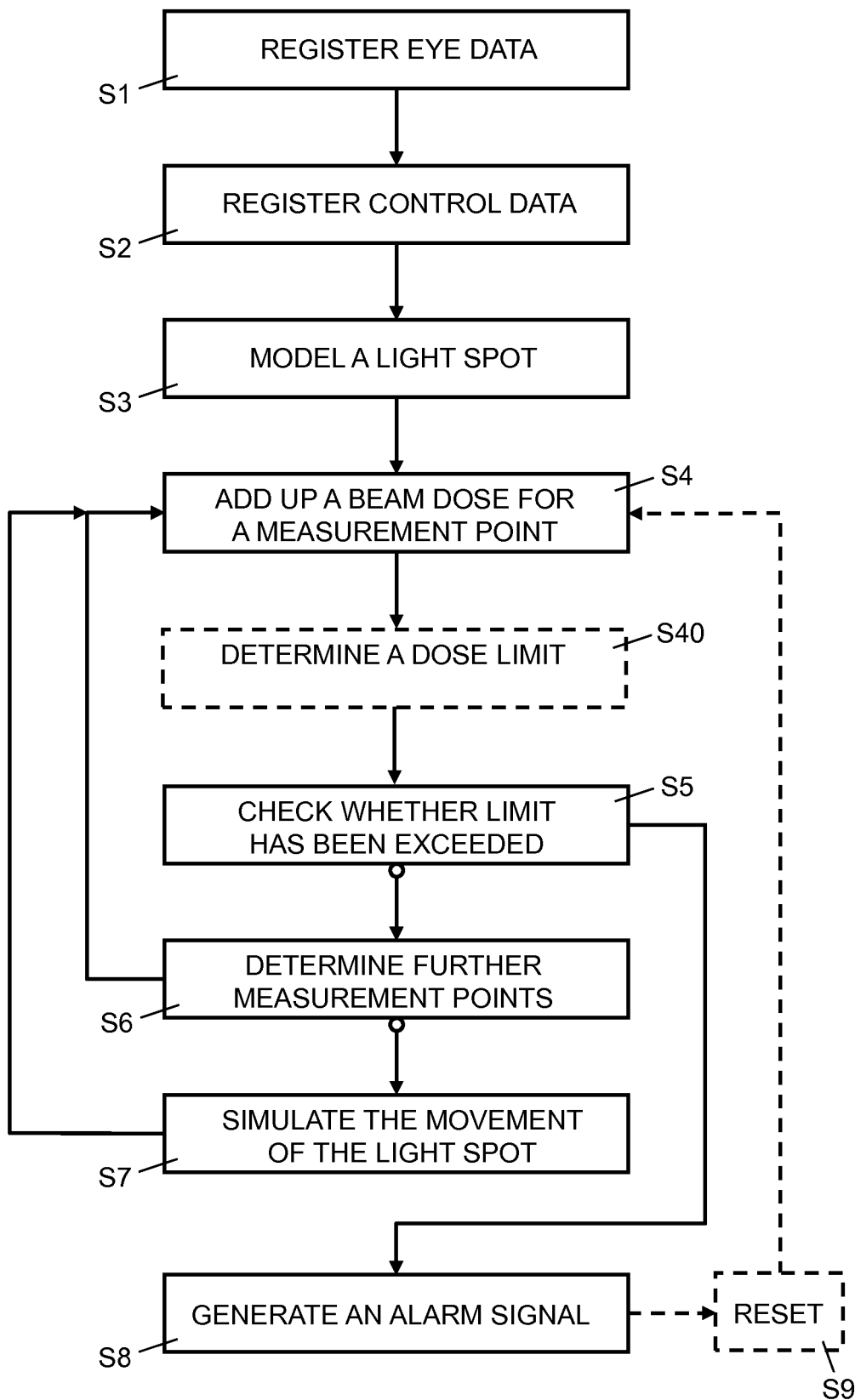
FIG. 2: shows a flowchart which illustrates, in an exemplary manner, a sequence of steps for protecting tissue when treating an eye with a laser beam.

In FIG. 1a, reference sign 1 relates to a device for protecting tissue when treating an eye 2 with a laser beam L generated by a laser system 31 of an optical therapy system 3 and deflected by a scanner system 32. Depending on the embodiment variant, the protection device 1 is arranged with the optical therapy system 3 in a common housing or arranged separately from the optical therapy system 3 in a dedicated housing.

In addition to the scanner system 32, the optical therapy system 3 comprises a laser system 31 with a laser source 310 and a control unit 30 for controlling the laser system 31, in particular for controlling the laser source 310 and the scanner system 32. The control unit 30 comprises a programmable processor with data and program memory. The laser source 310 is configured to generate a pulsed laser beam L, in particular with femtosecond laser pulses. Here, laser and beam parameters such as laser power, beam power of the laser beam L, pulse width, pulse rate, pulse energy, pulse intensity and/or laser beam intensity profile are adjustable by the control unit 30. By way of example, the scanner system 32 comprises displaceable optical units and/or one or more movable (e.g. rotatable) mirrors for deflecting the laser beam L in accordance with a scanning pattern and with a scanning speed, which are definable by the control unit 30. The focal size and divergence of the laser beam L provided for focused projection are also adjustable in the laser system 31 by way of the control unit 30. Depending on the embodiment, the scanner system can also contain the means for focusing and beam forming.

The protection device 1 comprises a processor 10, a control data module 11 and an eye model 12. The processor 10 comprises an integrated circuit, which is embodied as e.g. programmable microprocessor or as a different programmable logic unit, e.g. as an ASIC (application-specific integrated circuit). The processor 10 comprises a data memory and is configured or programmed in such a way that it executes the functions, described below, for protecting eye tissue during laser treatments.

The eye model 12 comprises eye data which define the dimensions, form and position of eye structures of the eye 2, e.g. of the cornea 21, epithelium, endothelium, iris 24, sclera, lens 22, front lens surface, rear lens surface and/or retinal surface 23 (retina). In one embodiment variant, the eye structures or surfaces of the eye structures are respectively modeled by a two-dimensional array A, wherein the array elements Axy respectively correspond to an area element or pixel of an eye structure or surface of the eye structure with an associated measurement point of the relevant eye structure or surface of the eye structure. The area elements or pixels are quadratic and have a length or width of 10 µm-500 µm. In the simplest form thereof, the array A corresponds to the cells of a grid arranged in a horizontal plane (extending normally in relation to the projection axis p), which is positioned in the vicinity of the relevant eye structure in the direction of the projection axis p, e.g. as tangential plane through an apex of the eye structure or at a center point or centroid of the eye structure along a center axis in the direction of the projection axis p. In the example of FIGS. 1a and 1b, the array A for modeling the retina 23 corresponds to the cells of a grid arranged on a plane extending normally to the projection axis p, said grid lying at a level a, which corresponds to the center point of the extent of the retina 23 in the direction of the projection axis p. In a more complicated variant, the array A corresponds to the measurement points of a grid placed onto the actual surface of the relevant eye structure, i.e. the individual array elements have different assigned heights or depths in the direction of the projection axis p. A plurality of eye structures or surfaces of eye structures are respectively modeled by a separate array A. By way of example, in addition to the retina 23, further arrays A are defined for the cornea and iris and the front and rear lens surface. In one embodiment variant, provision is made for a three-dimensional array, the array elements of which each correspond to a volume element or voxel of the eye 2 with an associated measurement point. The volume elements or voxels are cubic and have an edge length of 10 μm-500 μm. In one variant, a three-dimensional eye model is defined by a plurality of tissue layers or corresponding arrays A lying above one another.

In one embodiment variant, the protection device 1 comprises a measurement system 14 configured to determine the eye data during the treatment of the eye 2, for example an interferometric measurement system coupled optically into the beam path of the optical therapy system 3. The processor 10 is configured to generate the eye model 12 on the basis of the eye data registered and supplied by the measurement system 14. In an alternative embodiment variant, the protection device 1 comprises a positioning system 15 configured to determine a relative position of the eye 2 during the treatment and to position an eye model, based on, and generated from, eye data registered prior to the treatment, in relation to the optical therapy system 3 depending on the relative position.

The control data module 11 is configured to register control data which define beam parameters of the laser beam L, e.g. the beam power of the laser beam L, a scanning pattern (two-dimensional xy-scanning pattern or three-dimensional xyz-scanning pattern) for the laser beam L and the scanning speed of the optical therapy system 3. Depending on the embodiment variant, the beam parameters of the laser beam L moreover comprise pulse width, pulse rate, pulse energy, pulse intensity, focal size, laser beam intensity profile $I(x)$ and divergence of the laser beam L. Within the scope of a so-called online configuration, the processor 10 registers the control data during the treatment of the eye 2 by the optical therapy system 3 or by the laser system 31 and/or scanner system 32, by way of example by way of a wireless or wired communication interface. In an offline configuration, the processor 10 registers the control data by way of a user interface 13 from a user, for example for simulating a treatment of the eye 2.

The processor 10 is configured, on the basis of the registered eye data and the registered or entered control data, to model by computation a light spot S moving on or in an eye structure 23 and to simulate the movement thereof. The modeling and simulating of light spots S is applied, in particular, to tissue layers which have a high absorption for the light wavelength of the laser beam L. As illustrated in FIGS. 1a, 1b, the processor 10 determines the outline and size of the light spot S on the eye structure, modeled by the array A, or the surface thereof on the basis of the beam cone C of the laser beam L or the divergence angle θ and the distance of the relevant eye structure from the focus F of the laser beam L. Here, the beam cone C or the divergence angle θ is dependent on the refractive index $n\_b$ of the medium downstream of the focus F. The position of the focus z is dependent on the refractive index $n\_a$ of the medium upstream of the focus F. For simplification purposes, values averaged for the media are assumed for the refractive indices $n\_a$ and $n\_b$. In a worst-case approach, media and interfaces are presumed which tend to generate the smallest spot on the retina. These relationships become more complex if even more media are situated in the system and intended to be taken into account, e.g. liquid in a patient interface filled with liquid, cornea, aqueous humor, lens body, vitreous humor, etc. The beams forming the cone are additionally deflected to the side if the interfaces between the media are at an angle. All of this is modeled by the eye model, which optionally also registers the region between the beam emergence at the light projector 33 of the optical therapy system 3 and the eye 2. Here, in a simple form, the calculation of the axis of the beam cone and the change of the cone angle are determined at each interface with the aid of Snell's law. In the case of forms deviating from the cone and in the case of relatively large critical angles, a number of rays of the beam are calculated by means of ray tracing methods and hence improved imaging is obtained.

Moreover, the processor 10 determines the intensity profile of the light spot S defined by the beam cone C on the basis of the intensity profile $I(x)$ of the laser beam L, for example a Gaussian intensity profile in the laser cross section of a Gaussian beam. As depicted on the right-hand side of FIG. 1b on the basis of the array portion A', shown in a magnified manner, the intensity profile $I(x)$ of the light spot S is imaged on the eye structure, for example in accordance with the resolution of the array A. In the case of a movement of the laser beam L, and, accompanying this, of the light spot S, the area elements of the eye structure represented by the array elements Axy are irradiated by different intensity values, which change with the movement.

Below, the steps performed by the processor 10 for protecting tissue when treating the eye 2 with the laser beam L generated by the laser system 31 and deflected by the scanner system 32 are described on the basis of an exemplary sequence with reference to FIG. 2.

In step S1, the processor 10 registers the eye data of the patient and thereupon, as described above, generates a corresponding eye model comprising one or more arrays A on the basis thereof.

In step S2, the processor 10, as described above, registers the control data which define the beam parameters of the laser beam L and the scanning pattern for the laser beam L.

In step S3, the processor 10, as described above, models the light spot S on the basis of the registered control data and on the eye structure(s) or the surface(s) thereof defined by the eye data. Here, the emergence angle of the laser beam L at the emergence window of the light projector 33 in respect of the projection axis p is determined by the scanner system 32 or the scanning pattern. The beam profile of the laser beam L or changes in the direction of the laser beam L are determined and modeled on the basis of the refractive indices $n\_a$ and $n\_b$ of the media situated upstream and downstream of the focus F. A person skilled in the art will understand that further structures or media in the beam path with the corresponding refractive indices and refractive values thereof can be taken into account when modeling and simulating the beam profile and the beam cone C and the light spots S emerging therefrom.

In step S4, the processor 10 registers the beam dose for the area elements of the eye structure covered or irradiated by the light spot S. Here, the beam dose emitted by the laser beam L in the array element Axy, which is associated with the relevant area element, is added, respectively in a manner dependent on the intensity profile I(x) of the light spot S at the relevant area element. The beam or irradiation dose is added up as energy value by integrating the beam power of the laser beam L at the relevant area element. Consequently, each array element Axy corresponds to a measurement point which is associated with the relevant area element of the eye structure.

In the optional step S40, the processor 10 moreover updates an accumulated irradiation time t for the measurement point. That is to say, the processor 10 establishes an irradiation time t for the measurement point, during which the relevant area element of the eye structure is irradiated by the modeled light spot S. For the measurement point or the area element, the processor 10 moreover calculates a changing dose limit $D_{max}$ which is dependent on the irradiation time t at the relevant measurement point or area element. In one embodiment variant, the processor 10 moreover calculates the dose limit $D_{max}$ for the measurement points in a manner dependent on the wavelength of the laser beam L. By way of example, the processor 10 calculates the dose limit $D_{max}$ for the measurement points in accordance with the following equation:

$$D_{max} = C \cdot t^{\frac{3}{4}},$$

where C is a constant dependent on the wavelength of the laser beam L and t is the irradiation time at the relevant measurement point.

In step S5, the processor 10 checks whether the beam dose, which is added in step S4 for the measurement point represented by the array element Axy, exceeds the defined dose limit $D_{max}$. If the dose limit $D_{max}$ is in fact exceeded, the processor 10 continues in step S8 with the generation of an emergency signal. Otherwise, the processor 10 determines whether further measuring points which are irradiated by the current light spot S are to be treated in step S6. Depending on the type of dose value, the generation of an alarm signal can either lead to a termination of the treatment or, in a further embodiment, to the interruption thereof. As depicted schematically with the optional step S9, the treatment is once again continued after an interruption after a predetermined wait time by resetting ("reset") the accumulated dose values. By way of example, in the case of ultra short pulse infrared laser, a typical dose limit $D_{max}$ is established with the equation above with C=10 J/cm² and t in seconds; more precise values can be determined e.g. using standards such as ANSI Z136.1 or ISO 15004.

If further (area elements covered by the light spot S and corresponding) measurement points are to be calculated, the processor continues therewith in step S4. Otherwise, the processor 10 continues in step S7 with the simulation of the movement of the light spot S.

In step S7, the processor 10 simulates the movement of the light spot S on the basis of the scanning speed and scanning patterns defined by the control data. To this end, the processor 10 simulates the deflected laser beam L in accordance with the scanning pattern defined by the control data. That is to say the processor 10 determines the alignment and the beam profile of the laser beam L, proceeding from the emergence window of the light projector 33, through the eye 2 or the eye structures thereof, determined by the eye data of the eye model 12, in a manner dependent on the deflection of the laser beam L, which is brought about by the scanner system 32 in accordance with the scanning pattern defined by the control data and the refractive indices n_a and n_b of the media situated upstream and downstream of the focus F, as is described above in conjunction with step S3. A person skilled in the art will understand that different time base values $t_{sim}$ for successive simulation steps, which are selected dependent on the deflection or scanning speed of the optical therapy system 3 and, secondly, on the desired resolution or size of the area elements, are selectable for simulating the deflection of the laser beam L and the movement, connected therewith, of the light spot S and for simulating the irradiation of area elements of the eye structures brought about by the moving light spot S. In one embodiment variant, the time base value $t_{base}$ of a simulation step corresponds to the time which the deflected laser beam L or the light spot S based thereon requires to pass over the length or width $d_{pixel}$ of an area element. Hence, the time base value $t_{base}$ in the case of a scanning speed $v_{scan}$ emerges as $t_{base} = d_{pixel}/v_{scan}$. If the time base value $t_{base}$ is selected to be greater than $d_{laser\ beam}/v_{scan}$ (in the case of a laser beam diameter $d_{laser\ beam}$), some array elements Axy on the path of the light spot S are no longer written-to. What is accepted in such a mode of operation is that the irradiation dose for the array elements Axy which are not or insufficiently written-to is additionally added to the elements which are illuminated at the relevant time step and registered in the array A. This type of undersampling corresponds to a pessimistic calculation of the irradiation dose values and is therefore uncritical, even if, as a result of this, the maximum permissible dose limit $D_{max}$ cannot actually be achieved during the treatment. In order to achieve a more realistic distribution of the irradiation dose, the distribution of the beam intensity of the laser beam L is convolved with the movement vector of the light spot S and the distribution distorted in this manner is written to the array elements Axy. Here, the movement vector defines the movement of the light spot S and corresponds to the displacement of corresponding points of the light spot S, e.g. the center of the light distribution, during a time step. Typical values for the time base values $t_{base}$ lie in the ms or vs range if the scan speeds $v_{scan}$ in the range of 0.1 to 10 m/s are present. On the basis of the new position of the moving light spot S, the processor 10, in step S4, updates the beam dose for the area elements of the eye structure covered or irradiated by the light spot S. That is to say the beam power of the laser beam L, dependent on the intensity profile I(x) of the light spot S at the relevant positions, is established for the array elements Axy associated with the relevant area elements and the laser energy irradiated into the area element or at the associated measurement point is calculated on the basis thereof and added as a beam dose to the relevant array element Axy.

If the accumulated beam dose of an array element Axy exceeds the dose limit $D_{max}$, the processor 10 generates an emergency signal in step S8. In the online configuration, in which the beam load simulated by the light spot S is registered (in real-time) during and with the real treatment of the eye 2, the processor 10 transmits the emergency signal for interrupting the treatment to the optical therapy system 3 or laser system 31 and/or scanner system 32, for example by stopping the generation of the laser pulses and/or closing a stop for blocking the laser pulses. Expressed differently, in the online configuration, the simulated radiation exposure is determined parallel to, and synchronized with, the real eye treatment actually being carried out. In the off-line configuration, in which the beam load simulated by the light spot S is registered for preparing the treatment of the eye 2, the processor 10 emits the emergency signal as a warning notification by way of the user interface 13, for example as a warning notification on a display.

Finally, it should be stated that although specific functional modules were associated with computer program code in the description and that the performance of steps was illustrated in a specific sequence, a person skilled in the art will understand that the computer program code can have different structures and the sequence of at least certain steps can be modified without in the process departing from the subject matter for which protection is sought.

The invention claimed is:

1. A device for protecting tissue when treating an eye using a laser beam generated by an optical therapy system and deflected by a scanner system, comprising:
an eye model comprising eye data which define dimensions and locations of eye structures, the eye structures being modelled by arrays comprising array elements which represent parts of the eye structures;
a control data module configured to register control data which define beam parameters of the laser beam and a scanning speed and a scanning pattern for the laser beam, the beam parameters including a laser beam intensity profile; and
a processor configured to simulate by computation a light spot moving on or in an eye structure on the basis of the eye data and the control data, by determining an intensity profile of the light spot, based on the laser beam intensity profile, and modelling the intensity profile of the light spot on the eye structures by adding different intensity values to array elements representing parts of the eye structures covered by the light spot, depending on a value of the intensity profile of the light spot at the part of the eye structure represented by the respective array element, and moving the light spot based on the scanning speed and scanning pattern defined by the control data, such as to add up, continuously with the moving light spot, for a plurality of measurement points of the eye structure, each measurement point represented by one of the array elements, a beam dose emitted at the relevant measurement point by the moving light spot and to generate an emergency signal if a dose limit $D_{max}$ is exceeded at one of the measurement points,
wherein the processor is configured to calculate the dose limit $D_{max}$ for the measurement points, using in each case an irradiation time at the relevant measurement point and a constant which is derived from beam parameters of the laser beam.

2. The device of claim 1, wherein the processor is configured to simulate the moving light spot with a movement speed based on the scanning speed.

3. The device of claim 1, wherein the beam parameters comprise the beam power of the laser beam and wherein the processor is configured to add up the beam dose at the measurement points, respectively as an energy value, by integrating the beam power of the laser beam from the light spot moving over the relevant measurement point.

4. The device of claim 1, wherein the processor is configured to establish, for the measurement points of the eye structure and continuously, the irradiation time resulting by the moving light spot.

5. The device of claim 1, wherein the processor is configured to define the dose limit $D_{max}$ for the measurement points in a manner dependent on the wavelength of the laser beam.

6. The device of claim 1, wherein the processor is configured to calculate the dose limit $D_{max}$ for the measurement points according to the equation $D_{max}=C \cdot t^{3/4}$ in each case, where C is the constant dependent on beam parameters of the laser beam and t is the irradiation time at the relevant measurement point.

7. The device of claim 1, wherein the processor is configured to simulate the deflected laser beam on the basis of the scanning pattern defined by the control data, to model the eye structure on the basis of the eye data, and to simulate the moving light spot on the basis of the simulated deflected laser beam and the modeled eye structure.

8. The device of claim 1, wherein the processor is configured to establish the moving light spot on a surface of the eye structure and to add up the beam dose resulting from the moving light spot for a plurality of measurement points on the surface of the eye structure.

9. The device of claim 1, wherein the processor is configured to determine the moving light spot and the measurement points on a surface of one or more eye structures from the following list: epithelium, endothelium, iris, sclera, front lens surface, rear lens surface and retinal surface.

10. The device of claim 1, wherein the device is connected to the optical therapy system and the scanner system and wherein the processor is configured to register the control data from the optical therapy system and from the scanning system during the treatment of the eye and to transmit the emergency signal for interrupting the treatment to the optical therapy system.

11. The device of claim 1, wherein the processor is configured to register the control data for simulating the treatment of the eye by way of a user interface and to output the emergency signal as a warning notification by way of the user interface.

12. The device of claim 1, wherein the control data define one or more beam parameters from the following list: pulse width, pulse rate, pulse energy, pulse intensity, focal size, laser beam intensity profile and divergence of the laser beam provided for the focused projection, and wherein the processor is configured to simulate the moving light spot on the basis of the one or more beam parameters.

13. The device of claim 1, further comprising a measurement system configured to determine the eye data during the treatment of the eye.

14. The device of claim 1, further comprising a positioning system configured to determine a relative position of the eye during the treatment and to position the eye model relative to the optical therapy system in a manner dependent on the relative position.

15. A method comprising:
providing an eye model comprising eye data, the eye data defining dimensions and locations of eye structures, the eye structures being modelled by arrays comprising array elements which represent parts of the eye structures;
providing a control data module configured to register control data, the control data defining beam parameters of the laser beam and a scanning speed and a scanning pattern for the laser beam, the beam parameters including a laser beam intensity profile; and
one or more processors configured to simulate by computation a light spot moving on or in an eye structure on the basis of the eye data and the control data, by determining an intensity profile of the light spot, based on the laser beam intensity profile, and modelling the intensity profile of the light spot on the eye structures by adding different intensity values to array elements representing parts of the eye structures covered by the light spot, depending on a value of the intensity profile of the light spot at the part of the eye structure represented by the respective array element, and moving the light spot based on a scanning speed and scanning pattern defined by the control data, such as to add up, continuously with the moving light spot, for a plurality of measurement points of the eye structure, each measurement point represented by one of the array elements, a beam dose emitted at the relevant measurement point by the moving light spot and to generate an emergency signal if a dose limit is exceeded at one of the measurement points, wherein the one or more processors is further configured to calculate the dose limit for the measurement points, using in each case an irradiation time at the relevant measurement point and a constant which is derived from beam parameters of the laser beam.

16. The method of claim 15, wherein the one or more processors is further configured to simulate the moving light spot with a movement speed based on the scanning speed.

17. The method of claim 15, wherein the beam parameters further comprise the beam power of the laser beam and wherein the one or more processors is further configured to add up the beam dose at the measurement points, respectively as an energy value, by integrating the beam power of the laser beam from the light spot moving over the relevant measurement point.

18. The method of claim 15, wherein the one or more processors is further configured to establish, for the measurement points of the eye structure and continuously, the irradiation time resulting by the moving light spot.

19. A device comprising:

an eye model comprising eye data, the eye data defining dimensions and locations of eye structures, the eye structures being modelled by arrays comprising array elements which represent parts of the eye structures;

a control data module configured to register control data, the control data defining beam parameters of the laser beam, the beam parameters including a laser beam intensity profile; and a processor configured to simulate by computation a light spot moving on or in an eye structure on the basis of the eye data and the control data, by determining an intensity profile of the light spot, based on the laser beam intensity profile, and modelling the intensity profile of the light spot on the eye structures by adding different intensity values to array elements representing parts of the eye structures covered by the light spot, depending on a value of the intensity profile of the light spot at the part of the eye structure represented by the respective array element, and moving the light spot based on the scanning speed and scanning pattern defined by the control data, such as to add up, continuously with the moving light spot, for a plurality of measurement points of the eye structure, each measurement point represented by one of the array elements, a beam dose emitted at the relevant measurement point by the moving light spot and to generate an emergency signal if a dose limit is exceeded at one of the measurement points, wherein the processor is further configured to calculate the dose limit for the measurement points, using in each case an irradiation time at the relevant measurement point and a constant which is derived from beam parameters of the laser beam.

* * * * *